(12) United States Patent
Kersh et al.

(10) Patent No.: US 11,798,434 B2
(45) Date of Patent: Oct. 24, 2023

(54) THREE-DIMENSIONAL KNEE MODEL WITH REALISTIC PHYSIOLOGICAL AND BIOMECHANICAL KNEE FUNCTION

(71) Applicant: The Board of Trustees of the University of Illinois, Urbana, IL (US)

(72) Inventors: Mariana Elizabeth Kersh, Mahomet, IL (US); Sam Walter Goldsmith, Evanston, IL (US); Sara Moshage, Utica, IL (US); Roberto Alonso Pineda Guzman, Santa Cruz de Yojoa (HN)

(73) Assignee: The Board of Trustees of the University of Illinois, Urbana, IL (US)

( * ) Notice: Subject to any disclaimer, the term of this patent is extended or adjusted under 35 U.S.C. 154(b) by 94 days.

(21) Appl. No.: 17/167,844

(22) Filed: Feb. 4, 2021

(65) Prior Publication Data

US 2021/0248924 A1     Aug. 12, 2021

Related U.S. Application Data

(60) Provisional application No. 63/115,262, filed on Nov. 18, 2020, provisional application No. 62/971,703, filed on Feb. 7, 2020.

(51) Int. Cl.
| | |
|---|---|
| *G09B 23/28* | (2006.01) |
| *G09B 23/32* | (2006.01) |
| *D02G 3/02* | (2006.01) |
| *D02G 3/44* | (2006.01) |
| *A61F 2/08* | (2006.01) |

(52) U.S. Cl.
CPC .............. *G09B 23/286* (2013.01); *A61F 2/08* (2013.01); *D02G 3/02* (2013.01); *D02G 3/448* (2013.01); *G09B 23/32* (2013.01); *D10B 2321/08* (2013.01)

(58) Field of Classification Search
CPC ...... G09B 23/286; G09B 23/32; G09B 23/36; A61F 2/08; D02G 3/02; D02G 3/448; D10B 2321/08
USPC ............................................ 623/13.11, 13.12
See application file for complete search history.

(56) References Cited

U.S. PATENT DOCUMENTS

| | | | | |
|---|---|---|---|---|
| 4,597,766 | A | * | 7/1986 | Hilal .................... A61L 27/3662<br>623/13.12 |
| 7,575,602 | B2 | * | 8/2009 | Amirouche ............ A61B 5/076<br>623/18.11 |

(Continued)

OTHER PUBLICATIONS

ASTM International, (2015) "ASTM D2256/D2256M-10. Standard Test Method for Tensile Properties of Yarns by the Single-Strand Method," *Annu. B. ASTM Stand.*, vol. D2256/D225, No. 10, pp. 1-13.

(Continued)

*Primary Examiner* — Hoang M Nguyen
(74) *Attorney, Agent, or Firm* — Leydig, Voit & Mayer, Ltd.

(57) ABSTRACT

Disclosed herein are methods of using spun synthetic fibers to model ligaments of a joint of an animal. Further disclosed are models of joints which comprise spun synthetic fibers used to model ligaments. In certain aspects, the models of joints can be used for instructional purposes, as phantom models for testing medical devices or as models for calibration of tools used in physiological and/or biomechanical measurement.

36 Claims, 13 Drawing Sheets

(56) References Cited

U.S. PATENT DOCUMENTS

| | | | |
|---|---|---|---|
| 2004/0024456 A1* | 2/2004 | Brown, Jr. | A61F 2/08 623/13.13 |
| 2010/0292791 A1* | 11/2010 | Lu | A61P 31/00 623/13.12 |
| 2011/0066242 A1* | 3/2011 | Lu | A61K 35/32 623/23.72 |
| 2012/0109166 A1* | 5/2012 | Melvin | A61F 2/0811 606/151 |

OTHER PUBLICATIONS

Birch, et al. (2012) "Specialization of tendon mechanical properties results from interfascicular differences," *J. R. Soc. 25 Interface*, vol. 9, No. 76, pp. 3108-3117.

Bozec et al. (2007) "Collagen fibrils: Nanoscale ropes," *Biophys. J.*, vol. 92, No. 1, pp. 70-75.

Davis et al. (1992) "A biodegradable composite artificial tendon," *J. Mater. Sci. Mater. Med.*, vol. 3, No. 5, pp. 359-364.

Fetfatsidis et al. (2012) "Using Abaqus/Explicit to Link the Manufacturing Process to the Final Part Quality for Continuous Fiber-Reinforced Composite Fabrics", Simulia Comminity Conference.

Freedman et al. (1998) "The adequacy of medical school education in musculoskeletal medicine," *J. Bone Jt. Surg.*—Ser. A, vol. 80, No. 10, pp. 1421-1427.

Gentleman et al. (2003) "Mechanical characterization of collagen fibers and scaffolds for tissue engineering," vol. 24, pp. 3805-3813.

Guzman et al. (Submitted Sep. 21, 2020; published Mar. 12, 2021) "Replication of the tensile behavior of knee ligaments using architected acrylic yarn" *Journal of the Mechanical Behavior of Biomedical Materials*, 118. pp. 1-7.

Hearle, J. W. S. (1965) "Theoretical Analysis of the Mechanics of Twisted Staple Fiber Yarns," *Text. Res. J.*, vol. 35, No. 12, pp. 1060-1071.

Hearle et al. (1969) Structural Mechanics of Fibers, Yarns, and Fabrics. New York: Wiley-Interscience, Chapter 7, p. 302, Figure 7.19 only.

Iannace et al. (1995) "Mechanical behaviour of composite artificial tendons and ligaments," *Biomaterials*, vol. 16, No. 9, pp. 675-680.

Kastelic et al. (1978) "The multicomposite structure of tendon," *Connect. Tissue Res.*, vol. 6, No. 1, pp. 11-23.

Kersh, Mariana. (2010) "Virtual biomechanical knee: A finite element ligament model with experimental validation," University of Wisconsin-Madison.

Le et al. (2007) "The low-stress tensile behaviour of single worsted yarns," *J. Text. Inst.*, vol. 98, No. 5, pp. 421-429.

Manich et al. (2000) "Viscoelastic 10 modeling of natural and synthetic textile yarns," *J. Appl. Polym. Sci.*, vol. 76, No. 14, p. 2062.

Martin et al. (2018) "Gauging force by tapping tendons", Nature Communications DOI: 10.1038/s41467-018-03797, pp. 1-9.

Provenzano et al. (2006) "Collagen fibril morphology and organization: Implications for force transmission in ligament and tendon," *Matrix Biol.*, vol. 25, No. 2, pp. 71-84.

Shearer et al. (2014) "X-ray computed tomography of the anterior cruciate ligament and patellar tendon," *Muscles. Ligaments Tendons J.*, vol. 4, No. 2, pp. 238-244.

Shearer et al. (2017) "The relative compliance of energy-storing tendons may be due to the helical fibril arrangement of their fascicles," pp. 2-8.

Svensson et al. (2011) "Mechanical properties of human patellar tendon at the hierarchical levels of tendon and fibril".

Van Wyk, C. M. (1946) "20—Note on the compressibility of wool," *J. Text. Inst. Trans.*, vol. 37, No. 12, pp. T285-T292.

Weiss et al. (1996) "Finite element implementation of incompressible, transversely isotropic hyperelasticity," *Comput. Methods Appl. Mech. Eng.*, vol. 135, No. 1-2, pp. 107-128.

Woo, S. L. Y. (1986) "Biomechanics of Tendons and Ligaments," *Front. Biomech.*, pp. 180-195.

Yahia et al. (1988) "Collagen structure in human anterior cruciate ligament and patellar tendon," *J. Mater. Sci.*, vol. 23, No. 10, pp. 3750-3755.

Yelin et al. (2016) "The burden of musculoskeletal diseases in the United States," *Seminars in Arthritis and Rheumatism*.

* cited by examiner

THREE-DIMENSIONAL KNEE MODEL WITH REALISTIC PHYSIOLOGICAL AND BIOMECHANICAL KNEE FUNCTION

CROSS-REFERENCE TO RELATED APPLICATIONS

This application claims the benefit of priority to U.S. Provisional Patent Application No. 63/115,262, filed Nov. 18, 2020 and U.S. Provisional Patent Application No. 62/971,703, filed Feb. 7, 2020, each of which is hereby incorporated by reference in its entirety.

BACKGROUND OF INVENTION

The burden of knee injuries due to their diagnosis, treatment and rehabilitation is significant and contributes to 25% of total lost workdays in adults. While knee pain is among the most frequently reported of joint pain complaints, there is a lack of retention of musculoskeletal assessment skills. Seventy-four percent of fourth-year medical students failed to demonstrate basic understanding of musculoskeletal problems (K. B. Freedman, J. Bernstein, "The adequacy of medical school education in musculoskeletal medicine", *Journal of Bone and Joint Surgery-Series A* 80 (10) (1998) 1421-1427 (1998); Yelin, S. Weinstein, T. King, "The burden of musculoskeletal diseases in the United States", *Seminars in Arthritis and Rheumatism* (2016)), mainly due to the lack of exposure to clinical cases in their training.

The current "gold" standard for knee ligament injury diagnosis involves a comparison of the laxity levels manually sensed by a clinician in the injured and healthy limb. Laxity exams are difficult to teach and learn due to test factors such as the patient being relaxed, amount of time elapsed since injury, and the skill of the examiner. These exams require physical hands-on practice in order to achieve proficiency, but are difficult to learn due to constraints on medical residents caused by work hour limits and low exposure to injured patients. The inclusion of a hands-on, biomechanically realistic knee simulator in medical education could address the knowledge and skills gap of clinicians by providing a means of consistent training and ultimately lead to improved care for patients.

The passive biomechanical behavior of the knee joint is characterized by the mechanical response of ligaments and the joint capsule to applied loads. Ligaments play an important role in this passive function, by connecting bones together, stabilizing the joint, and transmitting forces. Their mechanical function is achieved by their collagenous components (P. P. Provenzano, R. Vanderby, Collagen fibril morphology and organization: Implications for force transmission in ligament and tendon, Matrix Biology 25 (2) (2006) 71-84 (2006)), which consist of a complex hierarchical structure of collagen molecules, fibrils, fibers and fascicles (J. Kastelic, A. Galeski, E. Baer, "The multicomposite structure of tendon", *Connective Tissue Research* 6 (1) (1978) 11-23 (1978)); yielding non-linear and viscoelastic tensile mechanical behavior (S. L.-Y. Woo, "Biomechanics of Tendons and Ligaments", *Frontiers in Biomechanics* (1986) 180-195 (1986)). This non-linear curve is characterized by a region of low and increasing stiffness called the toe region, and a linear region where the ligament reaches a constant peak stiffness (FIG. 1).

A material construct capable of replicating this non-linear mechanical behavior is needed to develop physiologically relevant biomechanical models of ligaments for use in a knee simulator. Biodegradable composite artificial tendons have been developed using a water-swollen poly(2-hydroxyethylmethacrylate)/poly(caprolactone) blend hydrogel matrix reinforced with poly(lactic acid) fibres (P. A. Davis, S. J. Huang, L. Ambrosio, D. Ronca, L. Nicolais, "A biodegradable composite artificial tendon", *Journal of Materials Science: Materials in Medicine* 3 (5) (1992) 359-364 (1992)). Others have developed ligament constructs made of hydrogel polymer matrix reinforced with bundles of polyethylene terephtalate (PET) fibers (S. Iannace, G. Sabatini, L. Ambrosio, L. Nicolais, "Mechanical behaviour of composite artificial tendons and ligaments", *Biomaterials* 16 (9) (1995) 675-680 (1995)). However, these constructs were designed for in vivo tissue engineering applications and are not appropriate for incorporation into a physical knee simulator. Commercially available musculoskeletal models are limited to aesthetic anatomy demonstrations and, to the best of our knowledge, are not based on physiological biomechanical properties.

Thus, there continues to be a need to develop physiologically accurate biomechanical models of ligaments for use in joint simulators generally, including human knee models in particular.

SUMMARY OF THE INVENTION

Disclosed herein are methods of using spun synthetic fibers to model ligaments of a joint of an animal. Further disclosed are models of joints which comprise spun synthetic fibers used to model ligaments. It is presently disclosed that spun synthetic fibers provide a surprisingly accurate biomechanical model for the load displacement properties of ligaments which exhibit a load vs. displacement relationship which may be characterized as a "J-shaped" curve. In certain aspects, it has been found that particular physical characteristics of spun synthetic fibers, including fiber twist angle and packing fraction, are important to providing physiologically accurate biomechanical load displacement properties for simulated ligaments.

1. A method of using a spun synthetic fiber to model a ligament of a joint of an animal comprising:
a. providing at least two solid bone modeling substrates, wherein a first bone modeling substrate models a bone positioned on the opposite side of the joint relative to a second bone modeling substrate;
b. selecting a spun synthetic fiber which has a load displacement curve comprising a first region closest to the y-axis having a slope less than 1 indicating low stiffness, a second region further from the y-axis than the first region with increasing slope indicating increasing stiffness, and a third region further from the y-axis than the second region with a constant slope greater than 1 indicating constant peak stiffness;
c. attaching a first end of the spun synthetic fiber to the first bone modeling substrate at a physiologically relevant position corresponding to ligament attachment to the first modeled bone and a second end of the spun synthetic fiber to the second bone modeling substrate at a physiologically relevant position corresponding to ligament attachment to the second modeled bone; and
d. repeating step c for at least two ligaments found in the joint of the animal.

2. The method of aspect 1, wherein prior to step c, the spun synthetic fiber is looped along a longitudinal axis to form at least one loop on each end of the longitudinal axis of the spun synthetic fiber and, in step c, the spun synthetic fiber is attached to each of the bone modeling substrates by the at least one loop on each end of the longitudinal axis of the spun synthetic fiber.

3. The method of aspect 1 or 2, wherein the looping of the spun synthetic fiber provides at least one loop region and at least one neck region along the length of the loop, wherein the neck region of the spun synthetic fiber is embedded in silicone.

4. The method of any one of aspects 1 to 3, wherein step b further comprises selection of a spun synthetic fiber having a fiber twist angle between 16 and 21 degrees.

5. The method of any one of aspects 1 to 4, wherein step b further comprises selection of a spun synthetic fiber having a packing fraction between 0.22 and 0.41.

6. The method of any one of aspects 1 to 5, wherein the spun synthetic fiber is comprised by a yarn.

7. The method of aspect 6, wherein the yarn is an acrylic yarn.

8. The method of any one of aspects 1 to 7, wherein the joint of an animal is the knee of a human.

9. A model 10 of a joint of an animal comprising a spun synthetic fiber 40 used to model a ligament of the joint of an animal comprising:
a. at least two solid bone modeling substrates, wherein a first bone modeling substrate 20 models a bone positioned on the opposite side of the joint relative to a second bone modeling substrate 30;
b. at least one spun synthetic fiber 40 which has a load displacement curve 100 comprising a first region 110 closest to the y-axis having a slope less than 1 indicating low stiffness, a second region 120 further from the y-axis than the first region with increasing slope indicating increasing stiffness, and a third region 130 further from the y-axis than the second region with a constant slope greater than 1 indicating constant peak stiffness; and
c. an attachment of a first end 44 of the spun synthetic fiber to the first bone modeling substrate 20 at a physiologically relevant position 52 corresponding to ligament attachment to the first modeled bone in the joint of the animal and an attachment of a second end 42 of the spun synthetic fiber to the second bone modeling substrate 30 at a physiologically relevant position 50 corresponding to ligament attachment to the second modeled bone in the joint of the animal.

10. The model of aspect 9, wherein the spun synthetic fiber is looped along a longitudinal axis 200 to form at least one loop 210, 212 on each end of the longitudinal axis of the spun synthetic fiber and the spun synthetic fiber is attached to each of the bone modeling substrates by the at least one loop on each end of the longitudinal axis of the spun synthetic fiber.

11. The model of aspect 9 or 10, wherein the looping of the spun synthetic fiber provides a loop region 220 and a neck region 230 along the length of the loop, wherein the neck region 230 of the spun synthetic fiber is embedded in silicone.

12. The model of any one of aspects 9 to 11, wherein the spun synthetic fiber has a fiber twist angle between 16 and 21 degrees.

13. The model of any one of aspects 9 to 12, wherein the spun synthetic fiber has a packing fraction between 0.22 and 0.41.

14. The model of any one of aspects 9 to 13, wherein the spun synthetic fiber is comprised by a yarn.

15. The model of any one of aspects 9 to 14, wherein the yarn is an acrylic yarn.

16. The model of any one of aspects 9 to 15, wherein the joint of an animal is the knee of a human.

17. The model of any one of aspects 9 to 16, wherein the model is designed for instructional purposes.

18. The model of any one of aspects 9 to 17, wherein the model is designed as a phantom model for testing medical devices.

19. The model of aspect 18, wherein the phantom model is a model of a human knee and is designed for testing orthopedic implant devices.

20. The model of aspect 18, wherein the phantom model is a model of a human knee and is designed for testing artificial ligaments.

21. The model of aspect 18, wherein the phantom model is a model of a human knee and is designed for MRI measurements of musculoskeletal microstructure.

22. The model of any one of aspects 9 to 17, wherein the model is designed for calibration of tools used for physiological measurements.

23. The model of aspect 22, wherein the model is designed for calibration of a tool which measures shear wave speed.

24. The model of aspect 23, wherein the model is designed for calibration of a shear wave tensiometer.

25. A method for calibrating a measurement tool for measuring the mechanical properties of a ligament or tendon using a model of an animal joint comprising a spun synthetic fiber used to model a ligament of the joint comprising:
a. providing at least two solid bone modeling substrates, wherein a first bone modeling substrate models a bone positioned on the opposite side of the joint relative to a second bone modeling substrate;
b. selecting a spun synthetic fiber which has a load displacement curve comprising a first region closest to the y-axis having a slope less than 1 indicating low stiffness, a second region further from the y-axis than the first region with increasing slope indicating increasing stiffness, and a third region further from the y-axis than the second region with a constant slope greater than 1 indicating constant peak stiffness;
c. attaching a first end of a spun synthetic fiber to the first bone modeling substrate at a physiologically relevant position corresponding to ligament attachment to the first modeled bone and a second end of the spun synthetic fiber to the second bone modeling substrate at a physiologically relevant position corresponding to ligament attachment to the second modeled bone;
d. repeating step c for at least two ligaments found in the joint of the animal; and calibrating the measurement tool based on the mechanical properties of the model of the joint of an animal.

26. The method of aspect 25, wherein prior to step c, the spun synthetic fiber is looped along a longitudinal axis to form at least one loop on each end of the longitudinal axis of the spun synthetic fiber and, in step c, the spun synthetic fiber is attached to each of the bone modeling substrates by the at least one loop on each end of the longitudinal axis of the spun synthetic fiber.

27. The method of aspect 26, wherein the looping of the spun synthetic fiber provides a loop region and a neck region along the length of the loop, wherein the neck region of the spun synthetic fiber is embedded in silicone.

28. The method of any one of aspects 25 to 27, wherein step b further comprises selection of a spun synthetic fiber having a fiber twist angle between 16 and 21 degrees.

29. The method of any one of aspects 25 to 28, wherein step b further comprises selection of a spun synthetic fiber having a packing fraction between 0.22 and 0.41.

30. The method of any one of aspects 25 to 29, wherein the spun synthetic fiber is comprised by a yarn.

31. The method of aspect 25, wherein the yarn is an acrylic yarn.

32. The method of any one of aspects 25 to 31, wherein the joint of an animal is the knee of a human.

33. The method of any one of aspects 25 to 32, wherein the tool measures shear wave speed.

34. The method of aspect 33, wherein the tool is a shear wave tensiometer.

DETAILED DESCRIPTION OF THE INVENTION

Figure 1:
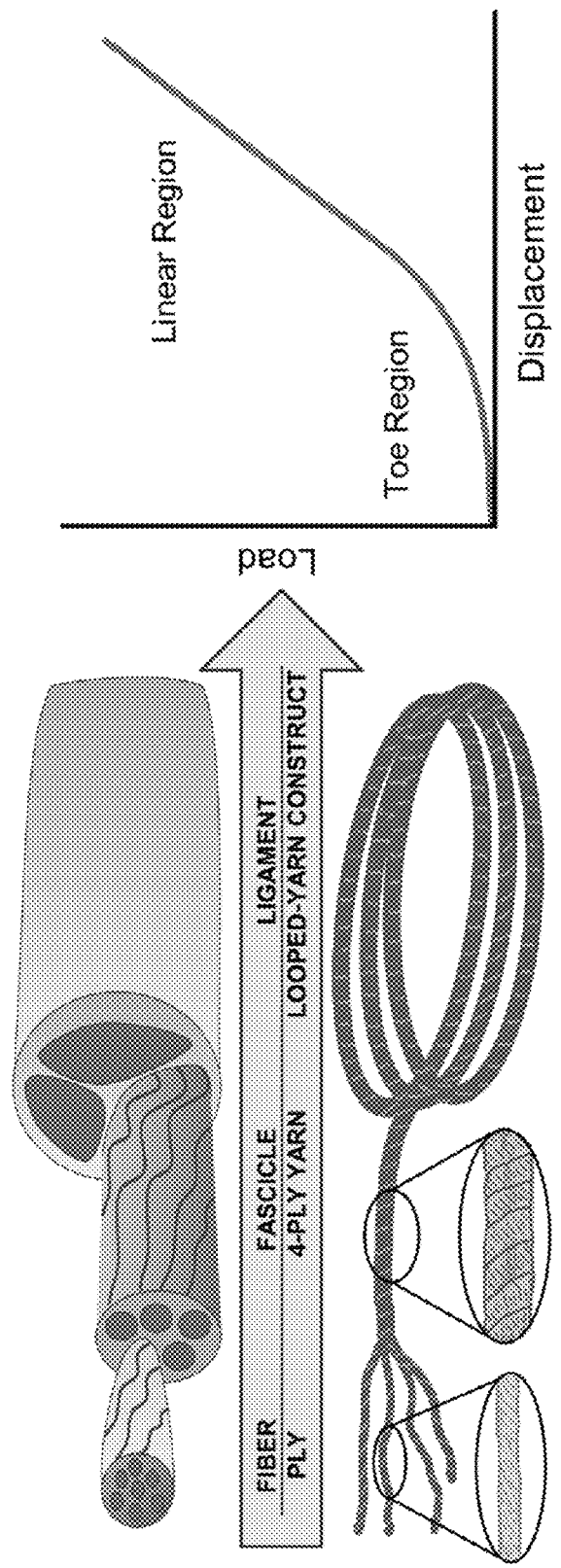
FIG. 1 illustrates hierarchical structure and load-displacement curve of knee ligaments and looped-yarn constructs.

While the present disclosure may be applied in many different forms, for the purpose of promoting an understanding of the principles of the disclosure, reference will now be made to aspects illustrated in the drawings and specific language will be used to describe the same. It will nevertheless be understood that no limitation of the scope of the disclosure is thereby intended. Any alterations and further modifications of the described aspects, and any further applications of the principles of the disclosure as described herein are contemplated as would normally occur to one skilled in the art to which the disclosure relates.

"Fiber twist angle", is used herein to refer to the angle at which constituent fibers of a spun synthetic fiber are twisted. The twist angle is measured relative to an axis defined by the longitudinal center (i.e. an axis evenly dividing a length) of the spun synthetic fiber.

"Load displacement curve", is used herein to refer to a line graph where Load is measured on the y-axis and Displacement of the material being tested is measured on the x-axis, wherein the relationship between load and displacement for the tested material is presented.

"Loop" or "looping", is used herein to define a curving or doubling over of a spun synthetic fiber to form a closed or partly open curve. In certain aspects, the looping provides for a loop region through which a fastener may be inserted and a neck region along which the fiber is doubled over.

"Packing fraction", is used herein to define a measure which results from dividing a spun synthetic fiber's cross-sectional area by the circular area calculated from the fiber's apparent diameter.

"Phantom model", is used here to refer to artificial structures designed to emulate properties of an animal body, in certain aspects a human body. Phantoms models may be used experimentally in lieu of, or as a supplement to, human subjects to maintain consistency, verify reliability of technologies, or reduce experimental expense.

"Physiologically relevant position", is used herein to refer to a position which provides utility with respect to physiological, biomechanical modeling. In certain aspects, physiologically relevant position is used herein to refer to the attachment point for a synthetic ligament.

"Solid bone modeling substrate", is used herein to refer broadly to any solid substrate, including any solid material, which may be used to model a bone. In certain aspects, a first solid bone modeling substrate may be used to model a femur and a second solid bone modeling substrate may be used to model a tibia, wherein the two are connected by a model ligament as disclosed herein. While in certain aspects, a solid bone modeling substrate may be selected to be a hard and inflexible material. A solid bone modeling substrate need not be hard and/or inflexible as long as the substrate provides the physiological and biomechanical bone modeling properties desired which can in certain aspects relate to flexibility, inflexibility, thickness, shape or any other physical feature of the bone being modeled.

"Spun synthetic fiber", is used herein to refer broadly to fibers produced by spinning. Spun synthetic fibers encompass spun artificial fibers and spun natural fibers. Regarding spun artificial fibers, the spinning process comprises extrusion, which may be performed with a spinneret, to form multiple continuous filaments which are twisted together. The spinning of spun artificial fibers may be in the form of wet, dry, dry jet-wet, melt, gel, and electrospinning. Regarding spun natural fibers, the spinning process comprises the drawing out of fibers and the twisting of fibers together. Spun artificial fibers or spun natural fibers can be wound on to a storage structure, optionally a spindle or cylinder (e.g. a bobbin).

Commercially available musculoskeletal models are limited to aesthetic anatomy demonstrations and are not based on physiological biomechanical properties. With the addition of biomechanically realistic passive components, the presently disclosed knee models replicate the passive biomechanical behavior of the knee joint.

The passive biomechanical behavior of the knee joint is characterized by the mechanical response of its passive components to applied loads. Ligaments play an important role in this passive function, by connecting bones together, stabilizing the joint, and transmitting forces. Their mechanical function is believed to be carried out by their collagenous components, which consist of a complex hierarchical structure of collagen molecules, fibrils, fibers and fascicles; yielding non-linear and viscoelastic mechanical behavior. This non-linear curve is characterized by a J-shaped region of low and increasing stiffness called the toe region, and a linear region where the ligament reaches its peak stiffness.

A material construct capable of replicating this non-linear mechanical behavior is needed to develop physiologically relevant biomechanical models of ligaments. Biodegradable composite artificial tendons have been developed using a water-swollen poly(2-hydroxyethylmethacrylate)/poly (capro-lactone) blend hydrogel matrix reinforced with poly (lactic acid) fibres. Others have developed ligament constructs made of hydrogel polymer matrix reinforced with bundles of poly-ethylene terephtalate (PET) fibres. These constructs were not designed to create knee physical models.

In an effort to identify a relevant collagen-surrogate, the inventors evaluated materials that have similar structural properties to ligaments with the rationale that these materials might also replicate ligament mechanical behavior. As disclosed herein, spun synthetic fibers with specified physical properties, serve as unexpectedly accurate collagen-surrogates providing similar structural properties to ligaments and replicating ligament biomechanical behavior (FIG. 1). In one aspect, under tension, spun yarn has a low-stiffness region at low strain levels due to yarn crimp, and then develops a linear region of maximum Young's modulus. Yarn's low stiffness region may be modeled as a function of the yarn's packing fraction and crimp angle. Similar to ligaments, spun yarn also exhibits viscoelastic properties. Based on study of the combination of J-shaped mechanical behavior, viscoelastic properties, and wide variety of materials and geometries, it is newly disclosed herein that spun synthetic fibers, e.g. yarn, can provide an appropriate foundation for the development of artificial ligaments.

Further disclosed herein, the effect of yarn's microstructure on its pre-yield stress behavior is characterized and its potential to replicate the J-shaped mechanical behavior of ligaments is described. To understand the physical grounds of the laxity levels found in yarn, a theoretical formulation of the low-stress tensile behavior of yarn was evaluated. In certain aspects, a single yarn may replicate the general shape of a ligament's mechanical behavior. In certain aspects, multiple yarn strands provide bulk for simulating a ligament's stiffness and strength. The configurations of different looped-yarn constructs were evaluated as well as their effect on laxity levels needed to replicate the mechanical behavior of knee ligaments.

Figure 7A:
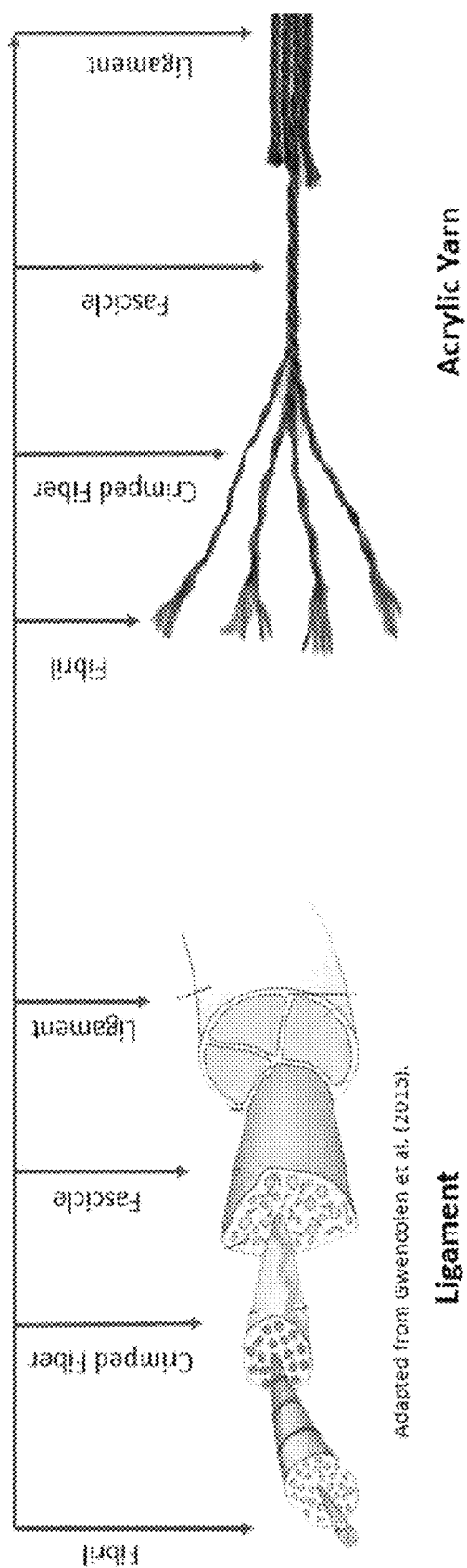
FIG. 7A illustrates the parallels between ligament and yarn structure.
Figure 7B:
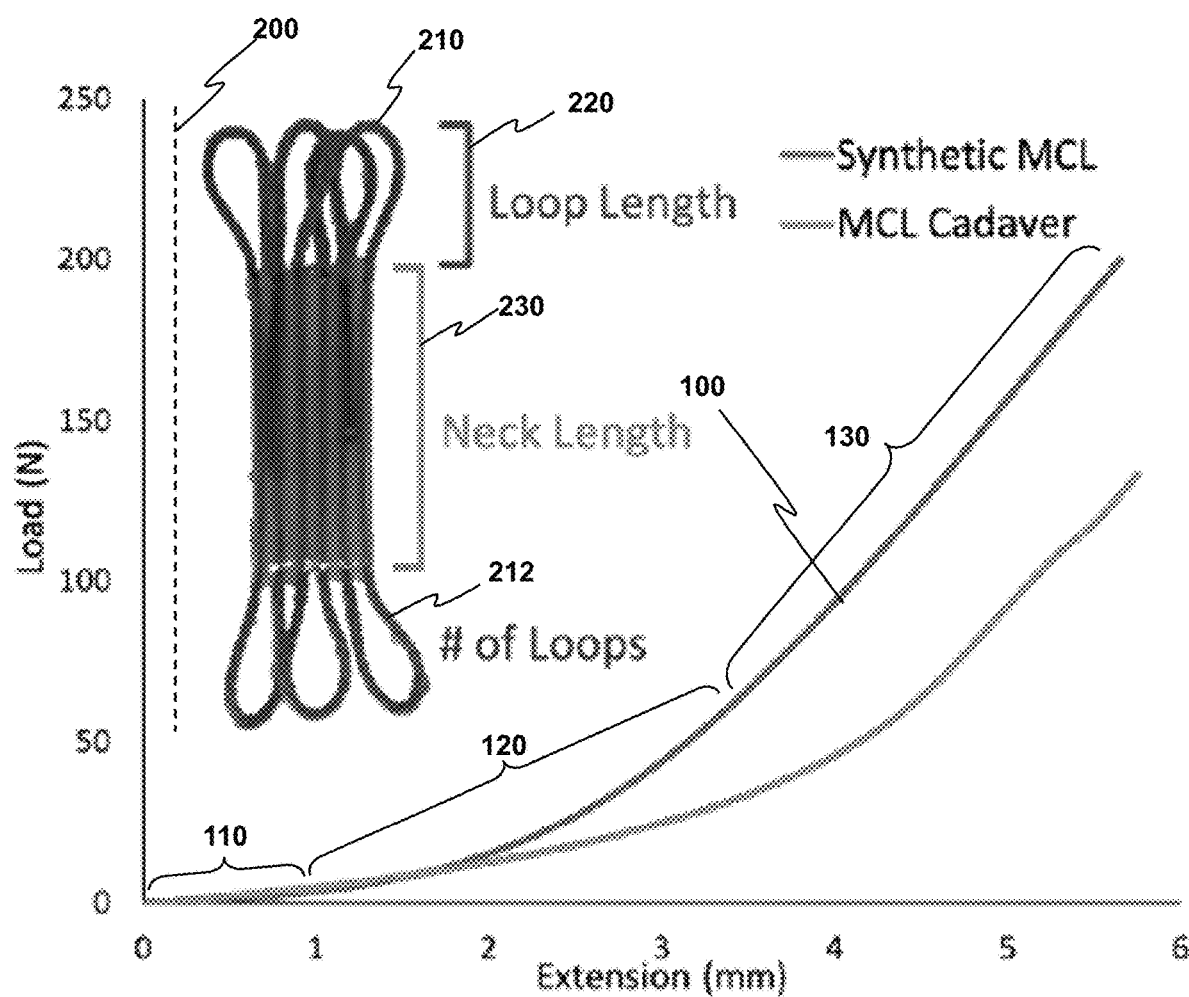
FIG. 7B illustrates load-displacement curves for a synthetic MCL in uniaxial tension and cadaver MCL in tension at 0° felxion.
Figure 7C:
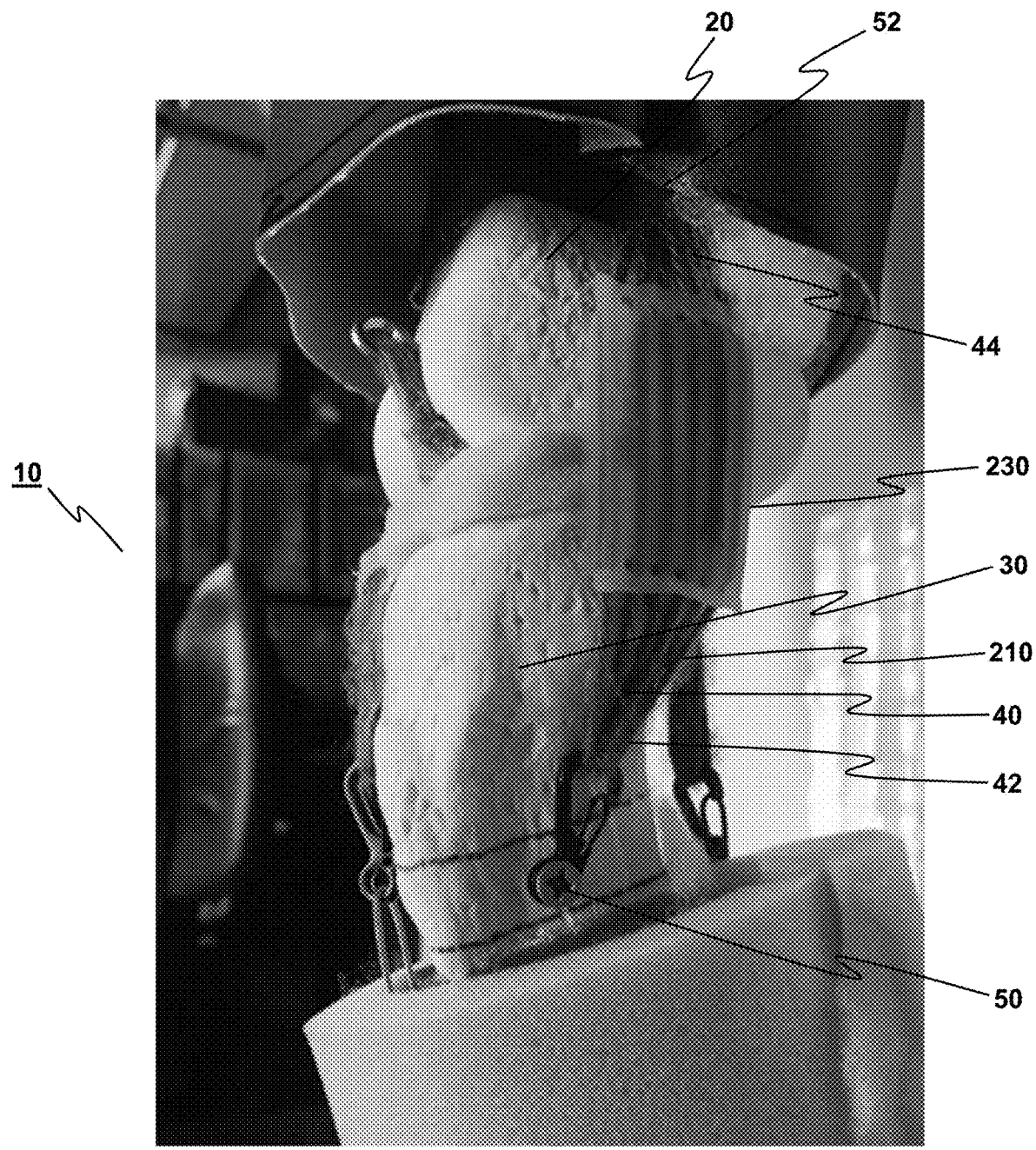
FIG. 7C shows an aspect of a synthetic ligament prepared with spun synthetic fibers as attached to modeled bones.

Aspects of the present disclosure include a 3D knee model comprising two masses that represent the femur and tibia bones. The two masses are interconnected by 4 composite material components representing the ligaments that compose the knee joint. In aspects of the present disclosure, the components are made up of 4-ply acrylic yarn strands embedded in a custom silicone rubber matrix. In aspects of the present disclosure, every ligament component has a different geometrical structure that allows it to recreate the specific mechanical properties of its respective knee ligament. In aspects of the present disclosure, the bone-ligaments-bone device has similar biomechanical properties to those of a cadaveric knee, simulating its mechanical response in a Lachman's test. Aspects of the present invention include a 3D knee model comprising yarn, embedded in silicone, dipped in petroleum jelly and bolted onto masses such as 3D printed bones. The yarn/silicone/petroleum jelly mix acts as an artificial ligament, and can be adjusted to reproduce the appropriate tension of a certain ligament by the number of loops and length of the neck, as is illustrated in FIGS. 7B and 7C, and as is discussed in additional detail below.

By studying the structural parameters of several multi-ply acrylic yarn constructs, the inventors aimed to characterize the effect of yarn's microstructure on its pre-yield stress behavior. By fitting their mechanical behavior into soft connective tissue models, the inventors aimed to relate a yarn's structural parameters with corresponding structural parameters of a knee ligament.

Even though a single yarn can replicate the general shape of a ligament's mechanical behavior, in some aspects, employing multiple yarn strands is preferable to obtain bulk ligament's stiffness and strength. To address this issue, aspects include looped-yarn constructs where the variation of loop number and length can be used to achieve the levels of laxity (toe length) and stiffness needed to replicate the mechanical behavior of knee ligaments. The inventors studied the effect of loop number and length on the constructs' mechanical behavior and demonstrate how the variation of these parameters can yield the mechanical behavior of any knee ligament (see FIG. 1).

By creating these synthetic ligament models, the creation of a passive biomechanical model is possible. The mechanical versatility of the looped yarn constructs is useful for the development of other joint models.

Four different types of medium gage 4-ply acrylic yarns were studied. Their mechanical behavior and structural parameters were quantified with high-resolution camera observations, micro computed tomography (micro CT) scans and uniaxial tension tests. Packing fraction and fiber twist were quantified because they have been related to the yarn's low-stress tensile behavior. The four yarn types were subjected to uniaxial tensile tests and the toe length, toe stiffness, and heel stiffness were measured from the resulting force-displacement curves. Microstructural parameters were related to the yarn's tensile mechanical properties to find the ideal yarn microstructure that mechanically replicates knee ligaments.

Certain suitable yarn to replicate knee ligament mechanics was uniaxially tested at the ply level and at a looped-construct level. The ply level tests were performed on ply-dissected yarns composed of 1, 2, and 3 plies. The looped-construct level tests were performed on yarn pieces looped 1-4 times around fixed rings and tied with a knot at the yarn piece's ends. Different loop length and loop numbers were tested.

Microscopic Observations

Figure 2A:
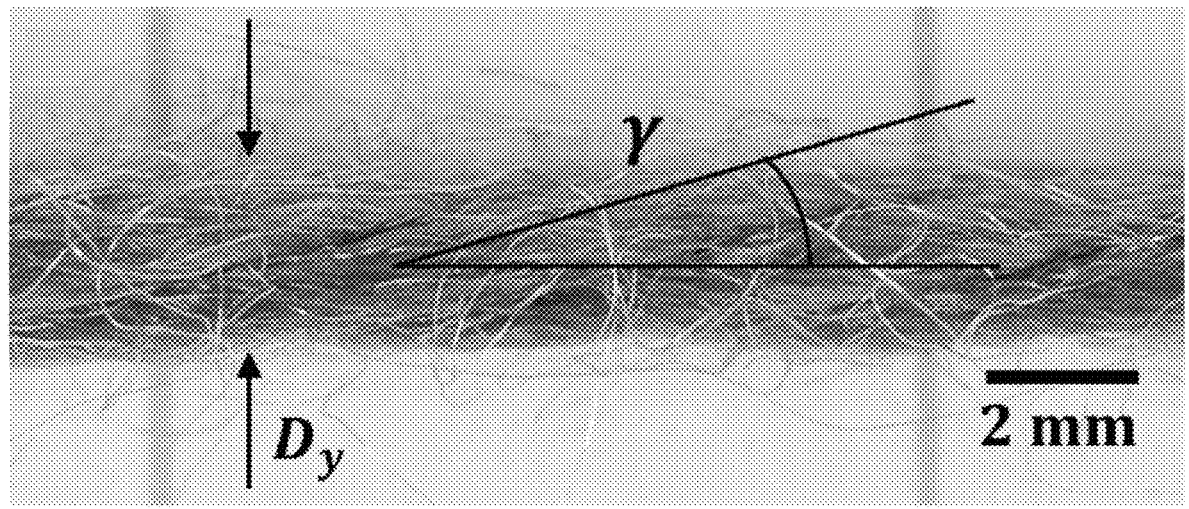
FIG. 2A illustrates measurement of yarn diameter, $D_y$, and ply twist angle, $\gamma$, on a yarn sample.
Figure 2B:
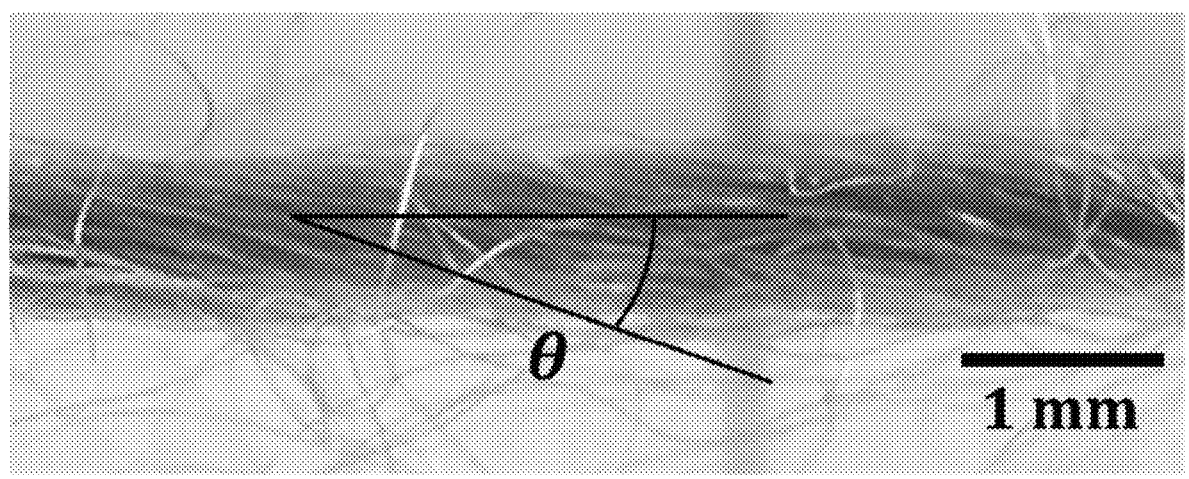
FIG. 2B illustrates measurement of fiber twist angle, $\theta$, on a ply sample.
Figure 3C:
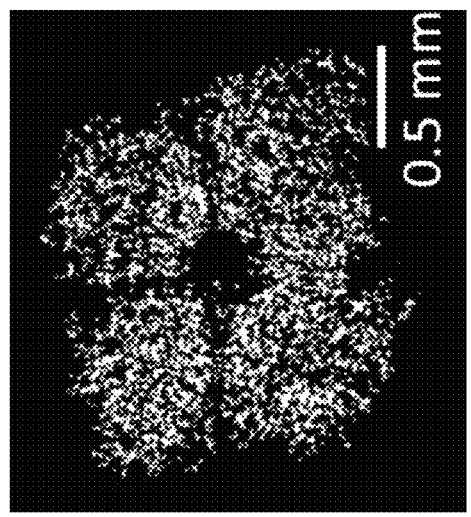
FIG. 3C shows a binarized image of a yarn's cross section.
Figure 3B:
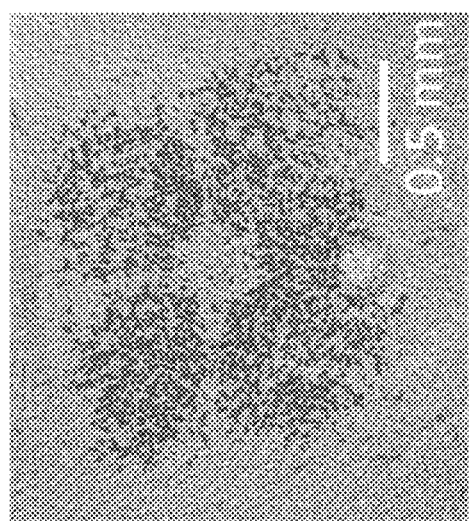
FIG. 3B shows segmented yarn voxels of the CT slice.
Figure 3A:
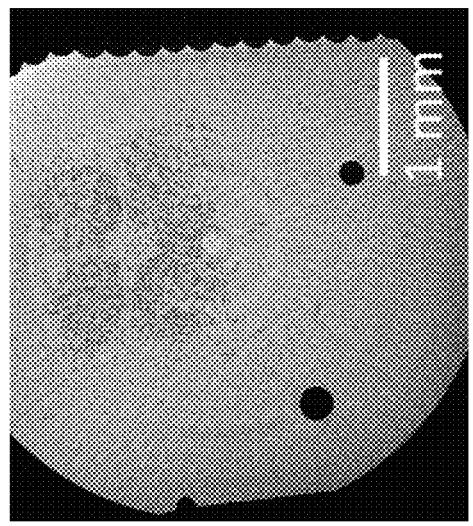
FIG. 3A shows a CT slice of a yarn's cross-section.

The yarn samples were structurally analyzed at a whole level and a ply level using images captured with a PHASEONE100 MP camera. Yarn diameter, ply diameter, ply twist angle, and fiber twist angle were obtained from the images using an image processing software (ImageJ). The yarns were stretched with an approximate load of 0.05+/−0.01 cN/tex to remove any slack. (See FIGS. 2A-2B)

Next, the yarns were embedded in a silicone resin to allow for microCT scanning (Xradia MicroCT, ZEISS) at a resolution of 4.4 μm. Using Amira and MATLAB, the yarn's packing fraction was obtained by dividing the area of all the cross-sectional fibers over the circular area calculated from the yarn's apparent diameter.

Mechanical Testing

All yarn samples and constructs were mechanically tested in tension using a universal testing machine (INSTRON) at a data collection frequency of 100 Hz. Following the ASTM D-2256 standard, the single 15 yarn tests were performed at a constant-displacement rate of 265 mm/min, which is the displacement rate necessary for a 250 mm long individual yarn sample to reach failure in 20+/−3 s. Prior to testing, samples were pre-tensioned to a load of 0.05+/−0.01 cN/tex to remove slack. While the ASTM standard suggested a pre-tension of 5 cN/tex, the standard was not designed to evaluate the toe region and we therefore chose to use a lower pre-tension value to preserve measurements of the toe region. Yarn ends were attached to the INSTRON's pneumatic grips using sandpaper to avoid sliding from the grips. All whole and dissected yarn samples were tested following the same procedure.

Looped-yarn constructs were assembled using screw eye attachments fixed to the Instron's grips. The constructs had a 0.3 N/loop pre-tension and were tested at a 265 mm/min displacement rate until reaching a load of 80 N/loop (approximate yield strength).

Data Processing

The force-displacement curve of each sample was analyzed using linear regression fits to the initial (toe) and linear (heel) sections of the force-displacement curve. The slope of each fit was defined as the toe and heel stiffness. The displacement value at the intersection of the toe and heel linear fits was considered the toe length of the force-displacement curve. The sample's toe length was divided over the sample's length to obtain the toe length's stretch ratio.

The force-displacement data of the yarn constructs was also fit to a strain energy function that represents the contribution of the collagen fiber family to the mechanical behavior of the knee ligament.

The packing fraction, and crimp angle of the yarn were input into a proposed function for the low-stress tensile behavior of worsted yarn. The modeled curves were compared to the original curves, with the objective of finding theoretical validation to our yarn selection.

Using Le and Phillips's equation 12 (C. V. Le and D. G. Phillips, *J. Text. Inst.*, vol. 98, no. 5, pp. 421-429, 2007), the crimp angle was obtained as a function of the initial crimp angle and the yarn's extension. The yarn uncrimping rate was obtained from this crimp parameter and compared to the parameter C4 of Weiss's equation (Equation 7.2) (J. A. Weiss, B. N. Maker, and S. Govindjee, *Comput. Methods Appl. Mech. Eng.*, vol. 135, no. 1-2, pp. 107-128, 1996) which is referred to as the uncrimping parameter of collagen fibers in ligaments.

Results

TABLE 1

Mechanical parameters measured on four different four-plied acrylic yarns

| Yarn Type | Toe Length [mm] | Toe Stiffness [N/mm] | Heel Stiffness [N/mm] |
| --- | --- | --- | --- |
| Type 1 | 35.6 (2.06) | 0.25 (0.008) | 1.50 (0.049) |
| Type 2 | 52.9 (3.63) | 0.36 (0.032) | 1.54 (0.086) |
| Type 3 | 17.0 (2.95) | 0.29 (0.074) | 1.05 (0.056) |
| Type 4 | 8.8 (0.48) | 0.43 (0.031) | 4.07 (0.111) |

Figure 5A:
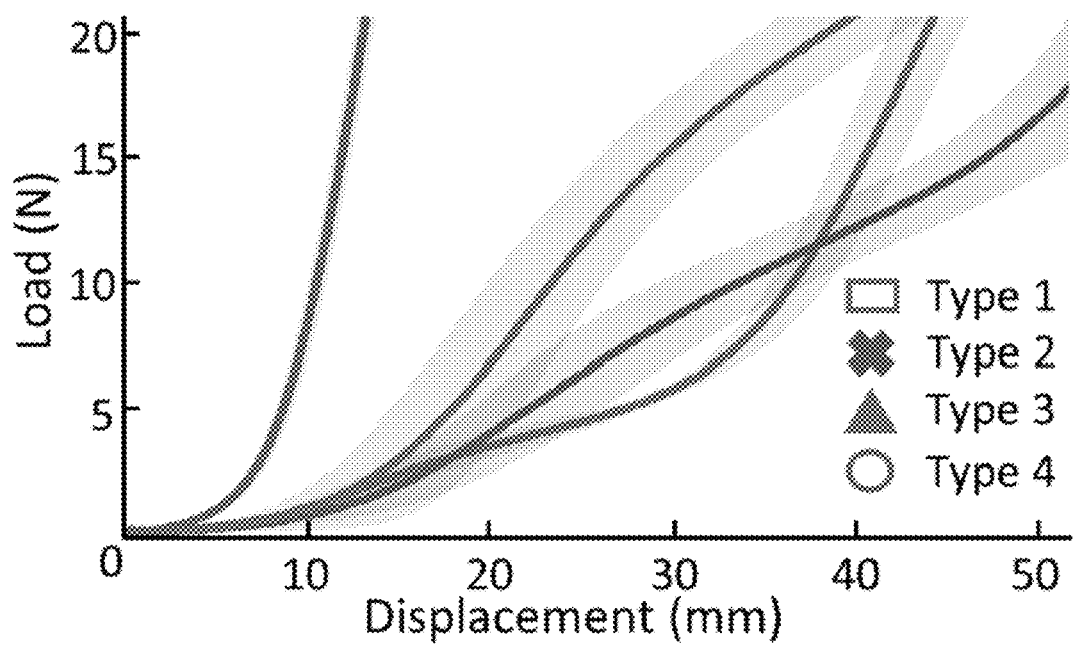
FIG. 5A shows the load-displacement curve of the 4 yarn types studied.

The 4 yarn types of Table 1 exhibit a load-displacement curve that begins with a toe region followed by a linear region reaching a peak stiffness (FIG. 5A). Yarn types 1 and 2 had toe regions with fluctuating stiffness that did not resemble the J-shaped load-displacement curve of a knee ligament in contrast to yarn types 3 and 4 which did exhibit a J-shaped toe region. Of these two yarns, yarn type 4 had the smallest and less variable toe length (8.54±0.53 mm, compared to 17.04±2.95 mm of yarn type 3).

Figure 5B:
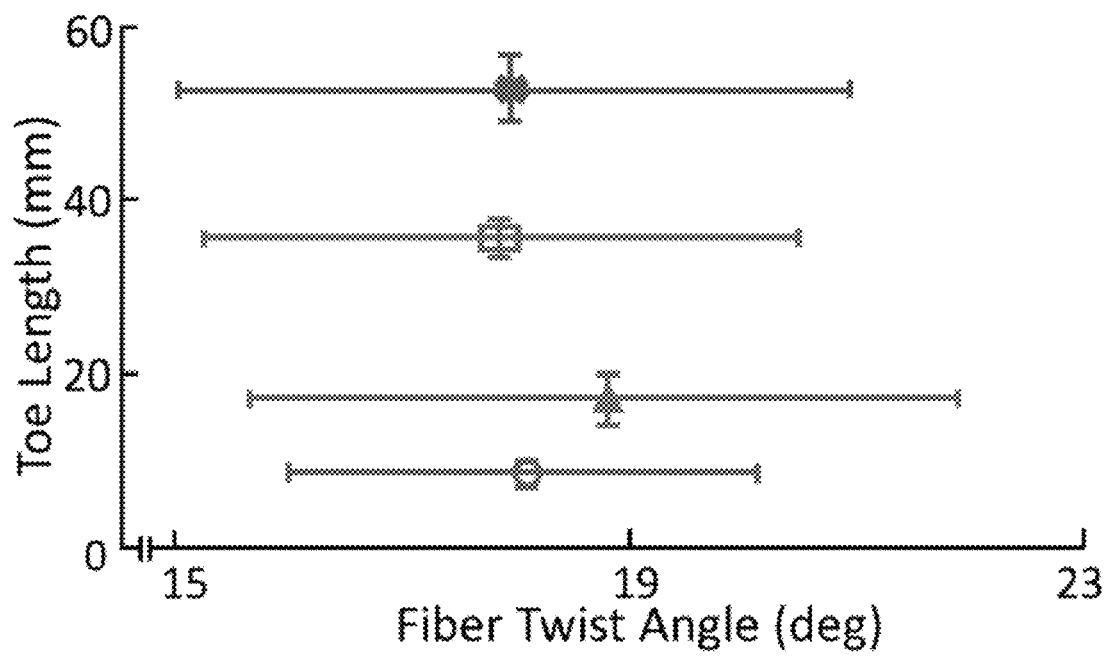
FIG. 5B shows experimental data relating to fiber twist angle and yarn's toe length.
Figure 5C:
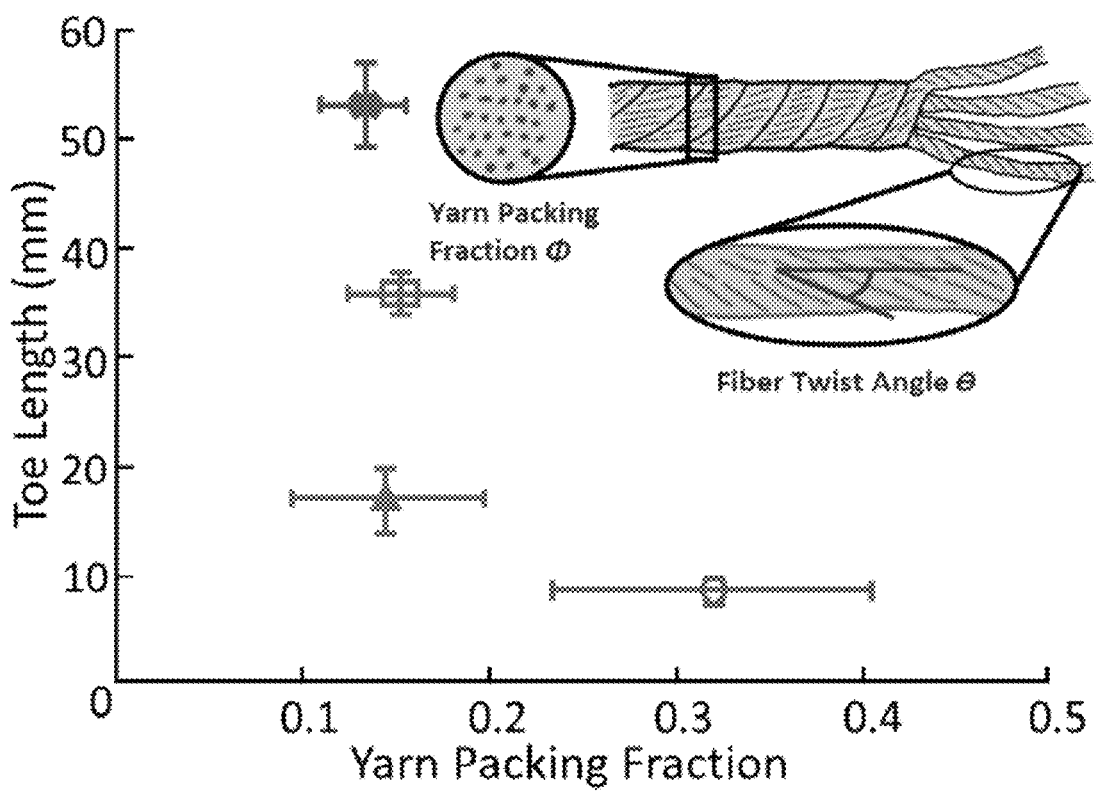
FIG. 5C shows experimental data relating to yarn packing fraction and yarn's toe length.
Figure 5D:
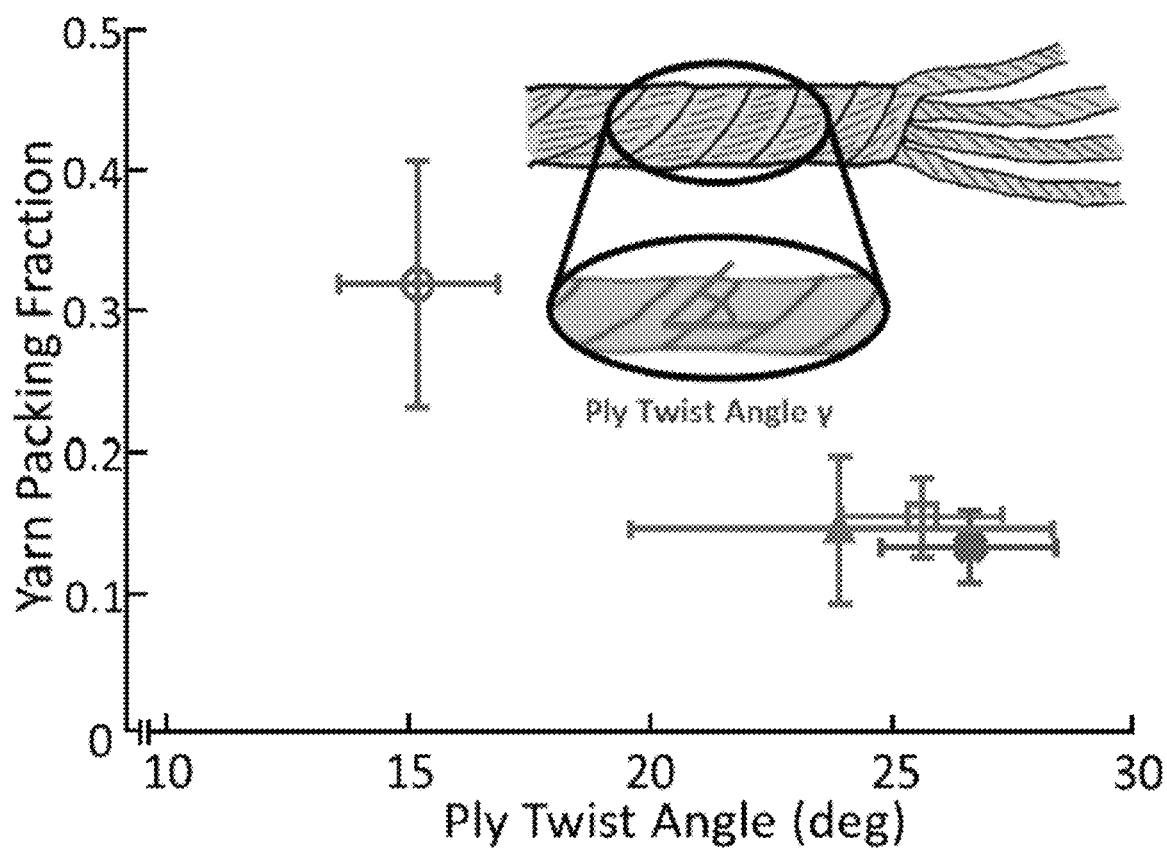
FIG. 5D shows experimental data relating to ply twist angle and yarn's packing fraction.

The fiber twist angle was similar amongst the different yarns (range=17.9-18.1°, FIG. 5B). Yarn type 4 had the highest packing fraction, $\phi$=0.32±0.08, which was double the mean packing fraction of the other yarn types (FIG. 5C). Yarn type 4 had the lowest ply twist angle (15.2±1.6 degrees) compared to the other 3 yarn types (range=23.9-26.6°, FIG. 5D). Yarn type 4 had the largest toe and heel stiffness of all yarn types tested (Table 1). Spun synthetic fibers may be selected with twist angles ranging from 15 to 22 degrees, 16 to 21 degrees, 17 to 20 degrees, 17 to 19 degrees, and within other ranges of twist angle as found to be useful for the methods and models disclosed herein. Further, spun synthetic fibers may be selected with packing fraction ranging from 0.20 to 0.43, 0.21 to 0.42, 0.22 to 0.41, 0.23 to 0.40, and within other ranges of packing fraction as found to be useful for the methods and models disclosed herein.

Figure 5E:
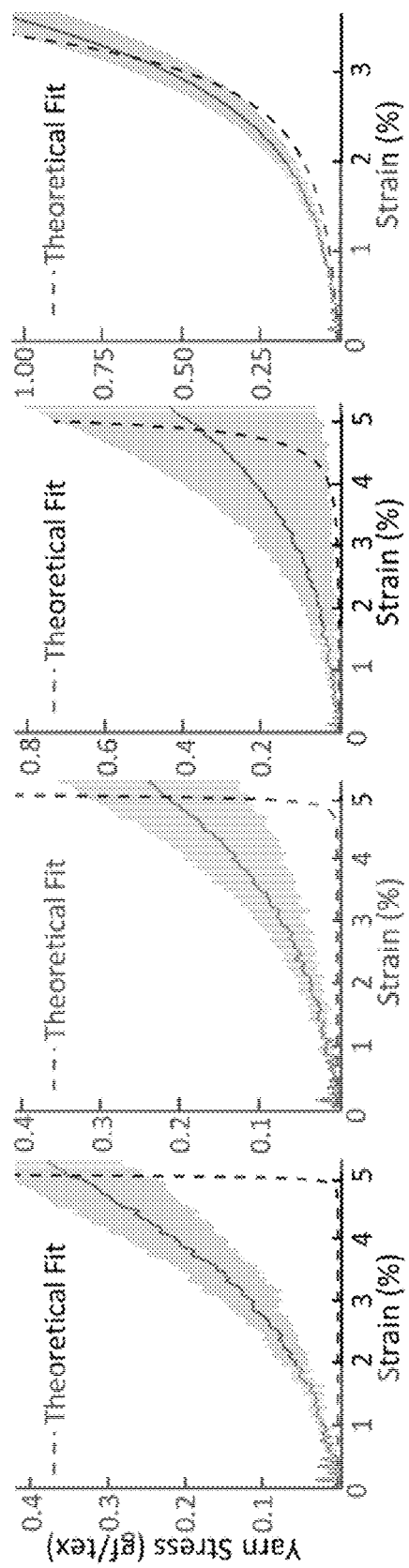
FIG. 5E shows experimental data relating to theoretical fits on the low stress-strain curve of the 4 yarn types.

The fit of the theoretical model of Equation 2 to the experimental stress-strain data of the different yarn types is shown in FIG. 5E. The fits on Yarn Types 1, 2, and 3 yielded $K_1Y$ values below 0.05 gf/tex, while the fit on Yarn Type 4 yielded a $K_1Y$ equal to 0.27 gf/tex.

Figure 6A:
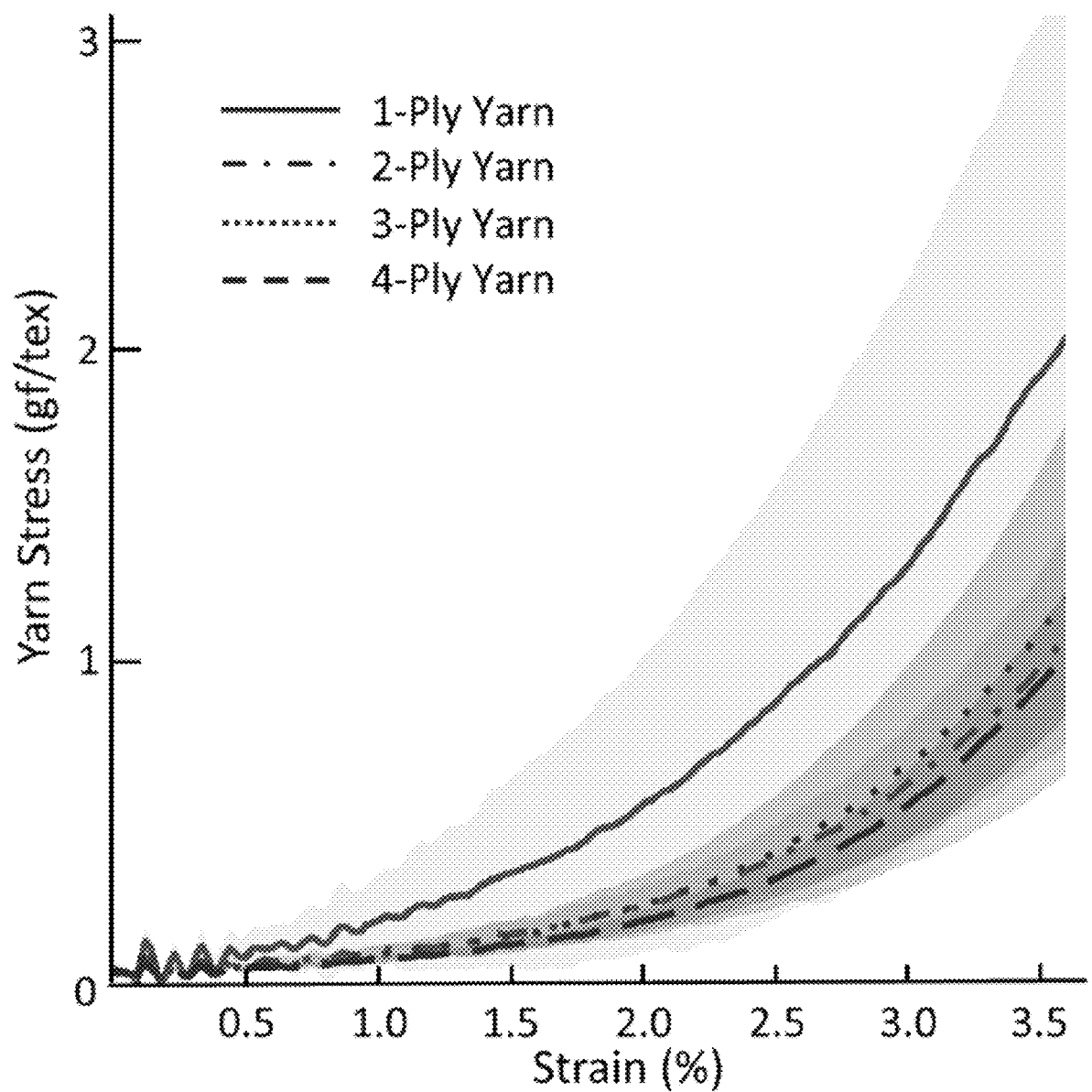
FIG. 6A shows the low stress-strain behavior of Yarn Type 4 at different ply levels.

Due to its J-shaped load-displacement curve, higher stiffness, and low toe length, Yarn Type 4 was used in looped-yarn constructs to replicate the load-displacement curve of knee ligaments. The stress-strain data from the mechanical tests performed on Yarn Type 4 at the different dissected-ply levels is plotted in FIG. 6A. The single ply was identified as the smallest structural unit where the J-shaped mechanical behavior was observed in our experiments. FIG. 6A also shows the decrease in mechanical variability and loss in load-carrying capacity introduced by the ply twisting.

Figure 6B:
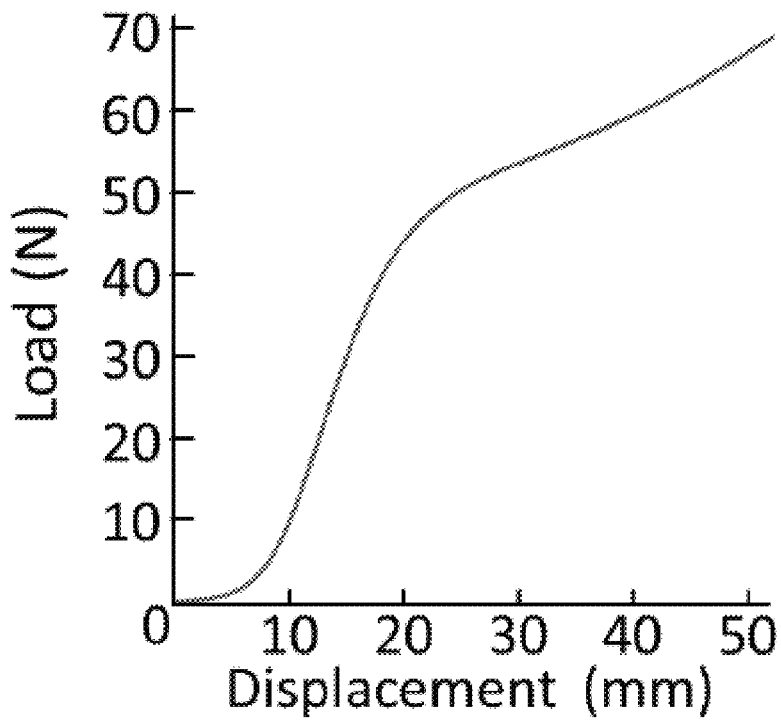
FIG. 6B shows the load-displacement curve of Yarn Type 4.
Figure 6C:
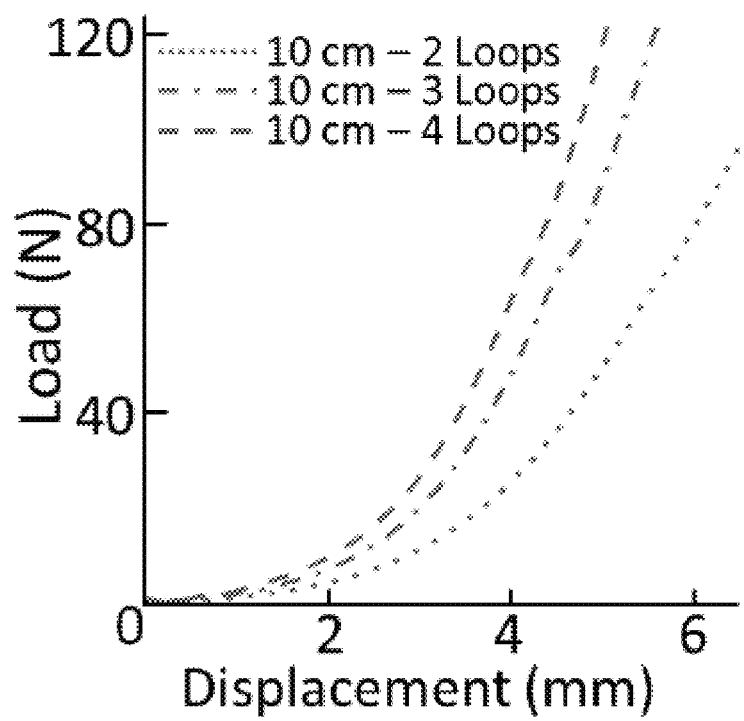
FIG. 6C shows the load-displacement curve of looped yarn constructs with different loop numbers.
Figure 6D:
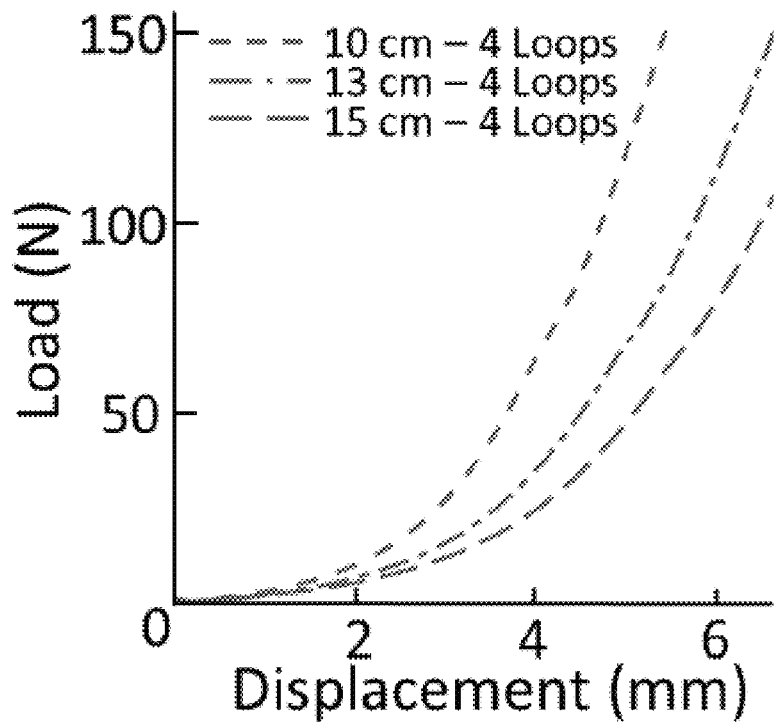
FIG. 6D shows the load-displacement curve of looped yarn constructs with different loop lengths.
Figure 6E:
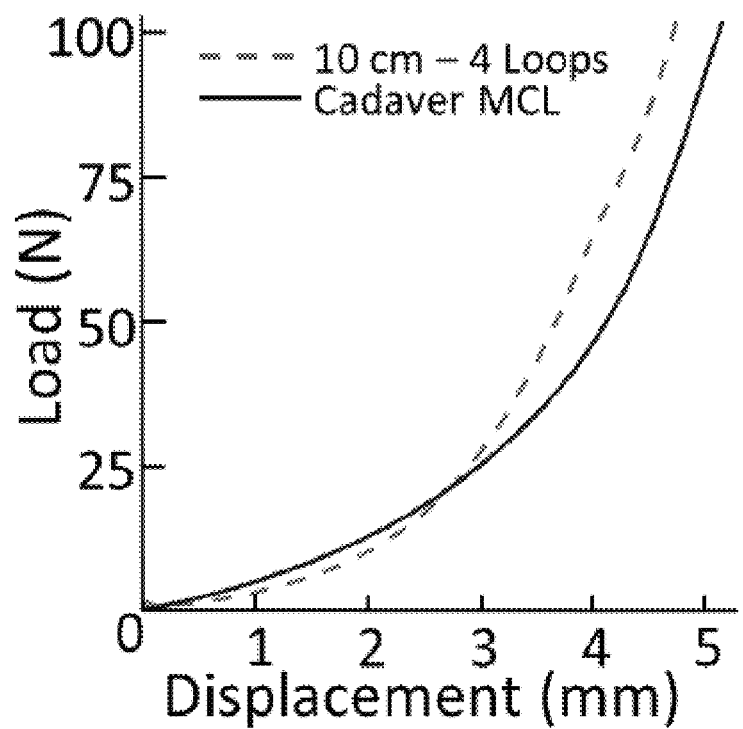
FIG. 6E shows a comparison between the load-displacement curve of a looped-yarn construct and a cadaver MCL.

The complete load-displacement curve of Yarn Type 4 is shown in FIG. 6B. At the looped-yarn level, an increase in loop number was associated with an increase in stiffness (FIG. 6C), and a decrease in loop length was associated with a decrease in toe length and an increase in stiffness (FIG. 6D). The toe strain of Yarn Type 4 remained close to 3.5% for all the ply and looped-yarn arrangements. The load-displacement data of a 10 cm, 4-looped yarn sample (Yarn Type 4) was compared to that of a cadaver medial col-lateral ligament, showing good agreement in most of the toe region and the start of the linear region (FIG. 6E).

The results from the disclosed acrylic four-plied yarn tensile experiments show how spun yarn can be used to replicate the mechanical behavior of knee ligaments. The crimp region of the spun yarn's load-displacement curve contributes to the desired mechanical behavior. The looped-yarn constructs provide for any desired level of laxity and stiffness of musculoskeletal tissues in a practical way.

The low-stress tensile behavior of spun yarns is ignored on the ASTM D-2256 standard. Yarn may be pre-loaded at 10% of the suggested standardized pre-load. During mechanical testing, it was observed that the yarn's toe region occurred during a diametrical compression of the yarn that induced a microstructural rearrangement of the fibers. Once the fiber rearrangement stopped, the linear or heel region was initiated on the load-displacement curve.

Spun yarn's low-stress tensile behavior can be characterized by the yarn's microstructural arrangement. Using Le and Phillip's mathematical formulation, the yarn's fiber twist angle and packing fraction are the parameters related to the low-stress tensile behavior or toe region of the tested acrylic yarn constructs. This theoretical formulation is suitable for low-stress tensile behaviors because it is based on Van Wyk's theory of fiber assembly compression.

Van Wyk's theory can be used because it assumes negligible friction forces, no extension and no slippage of the fibers; assumptions that hold in some yarns at the early stage of diametrical compression (E. Gentleman, A. N. Lay, D. A. Dickerson, E. A. Nauman, G. A. Livesay, and K. C. Dee, vol. 24, pp. 3805-3813, 2003). However, the mathematical model (Equation 2) derived from van Wyk's theory wasn't able to fit the stress-strain curve of Yarn Types 1, 2, and 3. It is believed that this happens because of the yarns' low packing fraction, which can lead to fiber slippage during fiber rearrangement in the toe region, leading to high strains during low stresses that produce singularities on equation 2. In Yarn Type 4, the toe region seems to be more smooth and adjusted to the theoretical fit. This is expected from Yarn Type 4 due to its high packing fraction, which can limit fiber slippage due to a higher fiber interaction during diametrical compression.

It appears that there's no standard value for the fiber modulus, Y, of acrylic fibers. There is some evidence that Y is equal to 5.14 gf/tex in acrylic fibers. In order for Yarn Type 4 to have a fiber modulus of 5.14 gf/tex, the fitting constant $K_1$ should equal to 0.052 (a value 70% smaller than the $K_1$ that fitted the stress-strain curve of wool fibers). Understanding the relationship between $K_1$ and yarns made from different fibers helps explain the effect of fiber material on the low-stress extensibility of a determined yarn type. Quantifying the fiber modulus Y of the fibers that compose a yarn and the fitting parameter $K_1$ of different yarn types, and testing more yarns will further strengthen the ability to apply or modify Equation 2 to predict different yarn type's low-stress tensile behavior.

In yarn literature, the relationship between a yarn's fiber twist angle, yarn diameter, and packing fraction is expressed as the yarn twist factor. The yarn twist factor is a design parameter in spun yarns, and it is usually related to the yarn's tenacity (tensile strength), breaking extension, and tensile modulus. The yarn's packing fraction can be controlled during yarn processing steps, based on the yarn spinning experience, to achieve the desired yarn properties.

Even though toe length is an important mechanical parameter of the artificial ligaments, controlling the heel stiffness also provides for good replication of a ligament's mechanical behavior.

The rope-like helical structure of plied yarn has been observed in collagen fibrils through Atomic Force Microscopy, in fascicles, and even in human anterior cruciate ligaments. Mechanically, Yarn Type 4 yielded a J-shaped load-displacement curve at all structural hierarchies, which is similar to tendon and ligament.

The mechanical behavior of tendon fascicles with helical fibril arrangement has been theoretically modeled and fitted to experimental data based on the fibril angle and fibril density, which are the same microstructural parameters disclosed herein to relate to the low-stress tensile behavior of yarn. It is believed that the consideration of the mechanical and structural framework of yarn in the study of the mechanics of soft collagenous tissues could yield a better explanation of the mechanical behavior at the tissue level in terms of its hierarchical collagenous microstructure.

By creating these synthetic ligament models, the creation of a passive biomechanical knee model is provided. The mechanical versatility of the presently disclosed looped yarn constructs is useful for the development of other joint models as well.

Example 1

Yarn Selection and Microscopic Observation

Four different 4-plied acrylic yarns with varying linear densities (Table 1) were evaluated with the aim of identifying different yarn microstructures and tensile behaviors.

The structure of the yarn samples was analyzed at the four-ply yarn level and at the ply level using images captured with a PHASEONE 100 MP camera (PHASEONE, Denmark). The yarns were stretched with an approximate load of 0.05±0.01 cN/tex prior to imaging to remove any slack. Yarn diameter, $D_y$, ply twist angle, γ, and fiber twist angle, e, was quantified (FIG. 2) as the mean of five independent measures of each parameter at different points along the length of the sample using image processing software (ImageJ, NIH).

Next, each yarn type was embedded in silicone resin (SMOOTHON, USA) for micro-Computed Tomography (μCT) scanning at an isotropic resolution of 5 μm (Xradia MicroCT, ZEISS, Germany). The yarn voxels were segmented from the resulting CT scan image using Amira (THERMO FISHER SCIENTIFIC, USA). The images were then binarized and the number of yarn pixels on each 2-D slice, n, was calculated (ImageJ, NIH). The fiber cross-sectional area, $A_f$, of each yarn type was then calculated by multiplying n by the square of the scan resolution, R. This process was repeated on five separate μCT scan slices per yarn type.

Packing fraction, ϕ, was measured by dividing the fibers' cross-sectional area by the circular area calculated from the yarn's apparent diameter, Dy, measured with the high-resolution images.

$$\Phi = \frac{4A_f}{\pi D_y^2} = \frac{4nR^2}{\pi D_y^2} \qquad \text{eq. 1}$$

Example 2

Mechanical Testing of Individual Yarn Samples

All yarn samples (n=5 per yarn type) were mechanically tested in tension using a universal testing machine (INSTRON, sampling frequency=100 Hz). Following the ASTM D-2256 standard for yarn, single yarn tests were performed on 250 mm long samples at a constant-displacement rate of 265 mm/min, the displacement rate necessary for the samples to reach failure in 20+/−3 s. Prior to testing, samples were pre-tensioned to a load of 0.5±0.1 cN/tex to remove slack. While the ASTM standard suggested a pre-tension of 5 cN/tex, the standard was not designed to evaluate the mechanical curve's toe region, therefore, use a lower pre-tension value was chosen to obtain the data of this part of the curve. The ends of the yarn were attached to the INSTRON's pneumatic grips using sandpaper and double-sided tape to avoid sliding.

Figure 4:
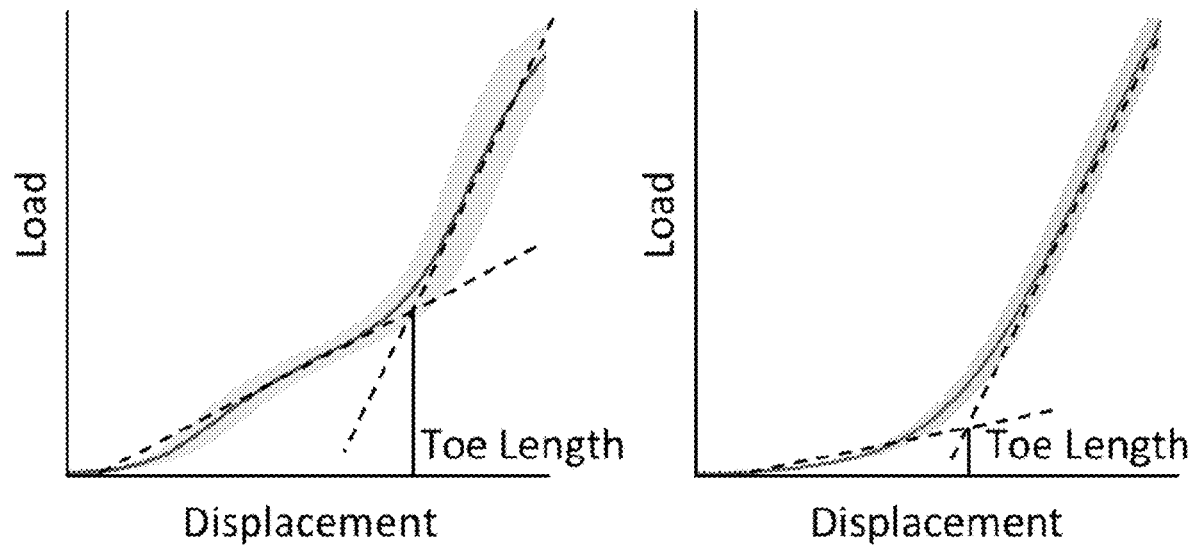
FIG. 4 shows the linear fits and toe length of the load-displacement curves of two different yarn types.

The load-displacement curve of each sample was analyzed using linear regressions to the initial (toe) and linear sections. The slope of each regression was defined as the toe and linear stiff-ness. The toe length of the curve was defined as the displacement value at the intersection of the toe and linear regressions (FIG. 4). Toe strain was calculated as the toe length divided by the sample's length.

Example 3

Theoretical Model of Low Stress Mechanics

The yarn packing fraction, $\phi$, and fiber twist angle, $\theta$, obtained from the four yarn types were used to evaluate a theoretical model of the low-stress tensile behavior of worsted yarn:

$$T = K_1 Y \Phi^3 \frac{\left\{\frac{1}{E+1} \times \frac{\sin^2\theta}{1-(E+1)^2 \cos^2\theta}\right\}^3 - 1}{\{1-(E+1)^2\cos^2\theta\}^{1/2} \times (E+1)\cos(\theta)} \qquad \text{eq. 2}$$

where T is the yarn tensile stress (Load/Linear Density), E is the yarn strain (Displacement/Sample Length), $K_1$ is a fitting constant based on fiber shape and distribution, and Y is the fiber's modulus. Due to a lack of standardized values for the $K_1$ and Y of acrylic yarns, Equation 2 was fitted to the low-stress mechanical data of each yarn using the lsqcurvefit function on MATLAB (MATHWORKS, USA). The stress-strain data of Yarn Types 1, 2, and 3 was fitted up to 5% strain (Equation 2 yields complex numbers when E>5%), and the stress-strain data of Yarn Type 4 was fitted up to its full toe length.

The modeled curves were compared to the experimental curves, with the objective of finding theoretical grounds for the yarn's low-stress tensile behavior, and understanding the limitations of this theoretical model to our application.

Example 4

Mechanical Testing—Looped Constructs

Finally, the yarn type that most closely matched the J-shaped curve characteristic of ligaments was evaluated at different hierarchical levels. To understand the contribution of different ply levels to our observation of the J-shaped mechanical curve, we dissected the yarn sample to individual 1-ply, 2-ply and 3-ply based samples and mechanically tested 10 samples of each ply number.

Looped-yarn constructs were assembled using screw eye attachments fixed to wooden parts attached to the INSTRON's grips. The constructs had a 0.3 N/loop pretension and were tested at a 265 mm/min displacement rate until reaching a load of 90 N/loop (approximate observed yield strength).

STATEMENTS REGARDING INCORPORATION BY REFERENCE AND VARIATIONS

All references throughout this application, for example patent documents including issued or granted patents or equivalents; patent application publications; and non-patent literature documents or other source material; including references 1-22 below, are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

REFERENCES

[1] E. Yelin, S. Weinstein, and T. King, "The burden of musculoskeletal diseases in the United States," Seminars in Arthritis and Rheumatism, 2016.

[2] K. B. Freedman and J. Bernstein, "The adequacy of medical school education in musculoskeletal medicine," J. Bone Jt. Surq.—Ser. A, vol. 80, no. 10, pp. 1421-1427, 1998.

[3] P. P. Provenzano and R. Vanderby, "Collagen fibril morphology and organization: Implications for force transmission in ligament and tendon," Matrix Biol., vol. 25, no. 2, pp. 71-84, 2006.

[4] J. Kastelic, A. Galeski, and E. Baer, "The multicomposite structure of tendon," Connect. Tissue Res., vol. 6, no. 1, pp. 11-23, 1978.

[5] S. L.-Y. Woo, "Biomechanics of Tendons and Ligaments," Front. Biomech., pp. 180-195, 1986.

[6] P. A. Davis, S. J. Huang, L. Ambrosio, D. Ronca, and L. Nicolais, "A biodegradable composite artificial tendon," J. Mater. Sci. Mater. Med., vol. 3, no. 5, pp. 359-364, 1992.

[7] S. lannace, G. Sabatini, L. Ambrosio, and L. Nicolais, "Mechanical behaviour of composite artificial tendons and ligaments," Biomaterials, vol. 16, no. 9, pp. 675-680, 1995.

[8] J. W. S. Hearle, P. Grosberq, and S. Backer, Structural Mechanics of Fibers, Yarns, and Fabrics. New York: Wiley-Interscience, 1969.

[9] C. V. Le and D. G. Phillips, "The low-stress tensile behaviour of single worsted yarns," J. Text. Inst., vol. 98, no. 5, pp. 421-429, 2007.

[10] A. M. Manich, P. N. Marino, M. D. de Castellar, M. Saldivia, and R. M. Sauri, "Viscoelastic 10 modeling of natural and synthetic textile yarns," J. Appl. Polym. Sci., vol. 76, no. 14, p. 2062, 2000.

[11] J. A. Weiss, B. N. Maker, and S. Govindjee, "Finite element implementation of incompressible, transversely isotropic hyperelasticity," Comput. Methods Appl. Mech. Enq., vol. 135, no. 1-2, pp. 107-128, 1996.

[12] ASTM International, "ASTM D2256/D2256M—10. Standard Test Method for Tensile Properties of Yarns by the Single-Strand Method," Annu. B. ASTM Stand., vol. D2256/D225, no. 10, pp. 1-13, 2015.

[13] R. B. Svensson et al., "Mechanical properties of human patellar tendon at the hierarchical levels of tendon and fibril," no. November, 2011.

[14] E. Gentleman, A. N. Lay, D. A. Dickerson, E. A. Nauman, G. A. Livesay, and K. C. Dee, "Mechanical characterization of collagen fibers and scaffolds for tissue engineering," vol. 24, pp. 3805-3813, 2003.

[15] H. L. Birch, P. D. Clegg, H. R. C. Screen, C. P. Udeze, and C. T. Thorpe, "Specialization of tendon mechanical properties results from interfascicular differences," J. R. Soc. 25 Interface, vol. 9, no. 76, pp. 3108-3117, 2012.

[16] M. E. Kersh, "Virtual biomechanical knee: A finite element ligament model with experimental validation," University of Wisconsin-Madison, 2010.

[17] C. M. van Wyk, "20—Note on the compressibility of wool," J. Text. Inst. Trans., vol. 37, no. 12, pp. T285-T292, 1946.

[18] J. W. S. Hearle, "Theoretical Analysis of the Mechanics of Twisted Staple Fiber Yarns," Text. Res. J., vol. 35, no. 12, pp. 1060-1071, 1965.

[19] L. Bozec, G. Van Der Heiiden, and M. Horton, "Collagen fibrils: Nanoscale ropes," Biophys. J., vol. 92, no. 1, pp. 70-75, 2007.

[20] L. H. Yahia and G. Drouin, "Collagen structure in human anterior cruciate ligament and patellar tendon," J. Mater. Sci., vol. 23, no. 10, pp. 3750-3755, 1988.

[21] T. Shearer et al., "X-ray computed tomography of the anterior cruciate ligament and patellar tendon," *Muscles. Ligaments Tendons J.*, vol. 4, no. 2, pp. 238-244, 2014.

[22] T. Shearer, C. T. Thorpe, H. R. C. Screen, and T. Shearer, "The relative compliance of energy-storing tendons may be due to the helical fibril arrangement of their fascicles," pp. 2-8, 2017.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred aspects, exemplary aspects and optional features, modification and variation of the concepts herein disclosed may be resorted to by those skilled in the art, and that such modifications and variations are considered to be within the scope of this invention as defined by the appended claims. The specific aspects provided herein are examples of useful aspects of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific aspects that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B." All references cited herein are incorporated by reference.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred aspects and optional features, modification and variation of the concepts herein disclosed may be resorted to by those skilled in the art, and that such modifications and variations are considered to be within the scope of this invention as defined by the appended claims.

We claim:

1. A method of using a spun synthetic fiber to model a ligament of a joint of an animal comprising:
   a. providing at least two solid bone modeling substrates, wherein a first bone modeling substrate models a bone positioned on the opposite side of the joint relative to a second bone modeling substrate;
   b. selecting a spun synthetic fiber which has a load displacement curve comprising a first region closest to the y-axis having a slope less than 1 N/mm indicating low stiffness, a second region further from the y-axis than the first region with increasing slope indicating increasing stiffness, and a third region further from the y-axis than the second region with a constant slope greater than 1 N/mm indicating constant peak stiffness;
   c. attaching a first end of the spun synthetic fiber to the first bone modeling substrate at a physiologically relevant position corresponding to ligament attachment to the first modeled bone and a second end of the spun synthetic fiber to the second bone modeling substrate at a physiologically relevant position corresponding to ligament attachment to the second modeled bone; and
   d. repeating step c for at least two ligaments found in the joint of the animal.

2. The method of claim 1, wherein prior to step c, the spun synthetic fiber is looped along a longitudinal axis to form at least one loop on each end of the longitudinal axis of the spun synthetic fiber and, in step c, the spun synthetic fiber is attached to each of the bone modeling substrates by the at least one loop on each end of the longitudinal axis of the spun synthetic fiber.

3. The method of claim 1, wherein the looping of the spun synthetic fiber provides at least one loop region and at least one neck region along the length of the loop, wherein the neck region of the spun synthetic fiber is embedded in silicone.

4. The method of claim 1, wherein the spun synthetic fiber has a fiber twist angle between 16 and 21 degrees.

5. The method of claim 1, wherein the spun synthetic fiber has a packing fraction between 0.22 and 0.41.

6. The method of claim 1, wherein the spun synthetic fiber is comprised of a yarn.

7. The method of claim 6, wherein the yarn is an acrylic yarn.

8. The method of claim 1, wherein the joint of the animal is a knee of a human.

9. A model of a joint of an animal comprising a spun synthetic fiber used to model a ligament of the joint of an animal comprising:
   a. at least two solid bone modeling substrates, wherein a first bone modeling substrate models a bone positioned on the opposite side of the joint relative to a second bone modeling substrate;
   b. at least one spun synthetic fiber which has a load displacement curve comprising a first region closest to the y-axis having a slope less than 1 N/mm indicating low stiffness, a second region further from the y-axis than the first region with increasing slope indicating increasing stiffness, and a third region further from the y-axis than the second region with a constant slope greater than 1 N/mm indicating constant peak stiffness; and
   c. an attachment of a first end of the spun synthetic fiber to the first bone modeling substrate at a physiologically relevant position corresponding to ligament attachment to the first modeled bone in the joint of the animal and an attachment of a second end of the spun synthetic fiber to the second bone modeling substrate at a physiologically relevant position corresponding to ligament attachment to the second modeled bone in the joint of the animal.

10. The model of claim 9, wherein the spun synthetic fiber is looped along a longitudinal axis to form at least one loop on each end of the longitudinal axis of the spun synthetic fiber and the spun synthetic fiber is attached to each of the bone modeling substrates by the at least one loop on each end of the longitudinal axis of the spun synthetic fiber.

11. The model of claim 9, wherein the looping of the spun synthetic fiber provides a loop region and a neck region along the length of the loop, wherein the neck region of the spun synthetic fiber is embedded in silicone.

12. The model of claim 9, wherein the spun synthetic fiber has a fiber twist angle between 16 and 21 degrees.

13. The model of claim 9, wherein the spun synthetic fiber has a packing fraction between 0.22 and 0.41.

14. The model of claim 9, wherein the spun synthetic fiber is comprised of a yarn.

15. The model of claim 14, wherein the yarn is an acrylic yarn.

16. The model of claim 9, wherein the joint of an animal is a knee of a human.

17. The model of claim 9, wherein the model is designed for instructional purposes.

18. The model of claim 9, wherein the model is designed as a phantom model for testing medical devices.

19. The model of claim 18, wherein the phantom model is a model of a human knee and is designed for testing orthopedic implant devices.

20. The model of claim 18, wherein the phantom model is a model of a human knee and is designed for testing artificial ligaments.

21. The model of claim 18, wherein the phantom model is a model of a human knee and is designed for MRI measurements of musculoskeletal microstructure.

22. The model of claim 9, wherein the model is designed for calibration of tools used for physiological measurements.

23. The model of claim 22, wherein the model is designed for calibration of a tool which measures shear wave speed.

24. The model of claim 23, wherein the model is designed for calibration of a shear wave tensiometer.

25. A method for calibrating a measurement tool for measuring the mechanical properties of a ligament or tendon using a model of an animal joint comprising a spun synthetic fiber used to model a ligament of the joint comprising:
   a. providing at least two solid bone modeling substrates, wherein a first bone modeling substrate models a bone positioned on the opposite side of the joint relative to a second bone modeling substrate;
   b. selecting a spun synthetic fiber which has a load displacement curve comprising a first region closest to the y-axis having a slope less than 1 N/mm indicating low stiffness, a second region further from the y-axis than the first region with increasing slope indicating increasing stiffness, and a third region further from the y-axis than the second region with a constant slope greater than 1 N/mm indicating constant peak stiffness;
   c. attaching a first end of a spun synthetic fiber to the first bone modeling substrate at a physiologically relevant position corresponding to ligament attachment to the first modeled bone and a second end of the spun synthetic fiber to the second bone modeling substrate at a physiologically relevant position corresponding to ligament attachment to the second modeled bone;
   d. repeating step c for at least two ligaments; and
   e. calibrating the measurement tool based on the mechanical properties of the model of the animal joint.

26. The method of claim 25, wherein prior to step c, the spun synthetic fiber is looped along a longitudinal axis to form at least one loop on each end of the longitudinal axis of the spun synthetic fiber and, in step c, the spun synthetic fiber is attached to each of the bone modeling substrates by the at least one loop on each end of the longitudinal axis of the spun synthetic fiber.

27. The method of claim 26, wherein the looping of the spun synthetic fiber provides a loop region and a neck region along the length of the loop, wherein the neck region of the spun synthetic fiber is embedded in silicone.

28. The method of claim 25, wherein the spun synthetic fiber has a fiber twist angle between 16 and 21 degrees.

29. The method of claim 25, wherein the spun synthetic fiber has a packing fraction between 0.22 and 0.41.

30. The method of claim 25, wherein the spun synthetic fiber is comprised of a yarn.

31. The method of claim 30, wherein the yarn is an acrylic yarn.

32. The method of claim 25, wherein the model of the animal joint is a model of a knee of a human.

33. The method of claim 25, wherein the tool measures shear wave speed.

34. The method of claim 33, wherein the tool is a shear wave tensiometer.

35. The method of claim 1, wherein the load displacement curve is obtained in accordance with ASTM D-2256.

36. The method of claim 1, wherein the first region has a slope less than 0.15 N/mm and the third region has a slope greater than 3.7 N/mm.

* * * * *